(12) United States Patent
Uchida et al.

(10) Patent No.: US 10,232,056 B2
(45) Date of Patent: Mar. 19, 2019

(54) METHOD FOR MEASURING TOXICITY OF HUMAN CSF

(71) Applicant: KYOWA HAKKO KIRIN CO., LTD., Tokyo (JP)

(72) Inventors: Shinichi Uchida, Tokyo (JP); Tomoyuki Kanda, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 15/304,292

(22) PCT Filed: Apr. 16, 2015

(86) PCT No.: PCT/JP2015/061765
§ 371 (c)(1),
(2) Date: Oct. 14, 2016

(87) PCT Pub. No.: WO2015/159963
PCT Pub. Date: Oct. 22, 2015

(65) Prior Publication Data
US 2017/0043039 A1    Feb. 16, 2017

Related U.S. Application Data

(60) Provisional application No. 61/980,206, filed on Apr. 16, 2014.

(51) Int. Cl.
| | | |
|---|---|---|
| *A61B 5/00* | (2006.01) | |
| *A61B 10/00* | (2006.01) | |
| *A61K 39/00* | (2006.01) | |
| *A61K 49/00* | (2006.01) | |
| *C07K 16/18* | (2006.01) | |
| *G01N 33/68* | (2006.01) | |

(52) U.S. Cl.
CPC ........ *A61K 49/0008* (2013.01); *A61B 5/4088* (2013.01); *C07K 16/18* (2013.01); *G01N 33/6896* (2013.01); *A61B 2010/0077* (2013.01); *A61B 2503/40* (2013.01); *A61B 2503/42* (2013.01); *A61K 2039/505* (2013.01); *C07K 2317/24* (2013.01); *C07K 2317/56* (2013.01); *C07K 2317/565* (2013.01)

(58) Field of Classification Search
CPC ......... A61K 2039/505; A61K 49/0008; G01N 33/6896; C07K 16/18; C07K 2317/24; C07K 2317/56; C07K 2317/565; A61B 2010/0077; A61B 2503/40; A61B 2503/42; A61B 5/4088
See application file for complete search history.

(56) References Cited

U.S. PATENT DOCUMENTS

| | | |
|---|---|---|
| 2010/0190803 A1 | 7/2010 | Shin et al. |
| 2012/0009179 A1 | 1/2012 | Kubota et al. |
| 2016/0067306 A1 | 3/2016 | Inoue et al. |

FOREIGN PATENT DOCUMENTS

| | | |
|---|---|---|
| JP | 2010-168344 A | 8/2010 |
| WO | 2005/067708 A2 | 7/2005 |
| WO | 2011016567 A1 | 2/2011 |
| WO | 2014171434 A1 | 10/2014 |

OTHER PUBLICATIONS

Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Epub Oct. 14, 2009.*
Hampel et al. The future of Alzheimer's disease: the next 10 years. Prog Neurobiol. Dec. 2011;95(4):718-28. Epub Nov. 22, 2011.*
Sankaranarayani et al. Altered neuronal activities in the motor cortex with impaired motor performance in adult rats observed after infusion of cerebrospinal fluid from amyotrophic lateral sclerosis patients. Behav Brain Res. Jan. 5, 2010;206(1):109-19. doi: 10.1016/j.bbr.2009.09.009. Epub Sep. 9, 2009.*
International Search Report dated Jul. 7, 2015, issued by the International Searching Authority in counterpart International Application No. PCT/JP2015/061765 (PCT/ISA/210).
Written Opinion dated Jul. 7, 2015, issued by the International Searching Authority in counterpart International Application No. PCT/JP2015/061765 (PCT/ISA/237).
Iryna Benilova, et al., "The toxic Aβ oligomer and Alzheimer's disease: an emperor in need of clothes", Nature Neuroscience, Mar. 2012, vol. 15, No. 3, pp. 349-357.
Kaj Blennow, "Biomarkers in Alzheimer's disease drug development", Nature Medicine, Nov. 2010, vol. 16, No. 11, pp. 1218-1222.
Marianne Renner, et al., "Deleterious Effects of Amyloid β Oligomers Acting as an Extracellular Scaffold for mGluR5", Neuron 66, Jun. 10, 2010, pp. 739-754.
Justin J. Yerbury, et al., "Extracellular chaperones modulate the effects of Alzheimer's patient cerebrospinal fluid on Aβ1-42 toxicity and uptake", Cell Stress and Chaperones (2010) vol. 15, pp. 115-121, DOI 10.1007/s12192-009-0122-0.
Erdem Yaka, et al., "Biological markers in cerebrospinal fluid (CSF) and evaluation of in vitro effect of CSF on PC12 cell line viability in Alzheimer's disease", Cell Biochemistry and Function, 2009, (Published online Jul. 28, 2009), vol. 27, pp. 395-401, DOI: 10.1002/cbf.1588.
Jeffrey P. Smith, et al., "Stimulus pattern dependence of the Alzheimer's disease amyloid-β 42 peptide's inhibition of long term potentiation in mouse hippocampal slices", Brainresearch, 2009, vol. 1269, pp. 176-184.

(Continued)

*Primary Examiner* — Gregory S Emch
(74) *Attorney, Agent, or Firm* — Sughrue Mion, PLLC (57) ABSTRACT

The problem is to provide a method that can quickly and efficiently evaluate the toxicity of human cerebrospinal fluid (CSF) with small amounts of human CSF. The problem is solved by a method comprising administering human CSF into the cerebral ventricle of a rodent such as a mouse, and evaluating the cognitive function of the rodent by using a behavioral pharmacological technique.

37 Claims, 3 Drawing Sheets

Specification includes a Sequence Listing.

(56) References Cited

OTHER PUBLICATIONS

Igor Klyubin, et al., "Amyloid β Protein Dimer-Containing Human CSF Disrupts Synaptic Plasticity: Prevention by Systemic Passive Immunization", The Journal of Neuroscience, Neurobiology of Disease, Apr. 16, 2008, vol. 28, No. 16, pp. 4231-4237.
Kara A. Kittelberger, et al., "Natural Amyloid-Beta Oligomers Acutely Impair the Formation of a Contextual Fear Memory in Mice", PLoS One, Jan. 2012, vol. 7, Issue 1, e29940, Total 7 pages.
Miranda N. Reed, et al., "Cognitive effects of cell-derived and synthetically derived Aβ oligomers", Neurobiology of Aging, 2011, vol. 32, pp. 1784-1794.
Tursun Alkam, et al., "A natural scavenger of peroxynitrites, rosmarinic acid, protects against impairment of memory induced by Aβ25-35", Behavioural Brain Research, 2007, vol. 180, No. 2, pp. 139-145.
R. M. Ridley, et al., "Very long term studies of the seeding of β-amyloidosis in primates", Journal of Neural Transmission, 2006, vol. 113, pp. 1243-1251, DOI 10.1007/s00702-005-0385-2.
Tarja Malm, et al., "β-Amyloid infusion results in delayed and age-dependent learning deficits without role of inflammation or β-amyloid deposits", PNAS, Jun. 6, 2006, vol. 103, No. 23, pp. 8852-8857.
R. Sankaranarayani et al., "Reach task-associated excitatory overdrive of motor cortical neurons following infusion with ALS-CSF", Journal of Neural Transmission, vol. 121, No. 1, Jul. 31, 2013, 11 pages total.
Search Report dated Aug. 17, 2017 by the European Patent Office in counterpart European Patent Application No. 15779412.4.

\* cited by examiner

SEQUENCE LISTING

<160> NUMBER OF SEQ ID NOS: 8

<210> SEQ ID NO 1

```
<211> LENGTH: 118
<212> TYPE: PRT
<213> ORGANISM: Artificial
<220> FEATURE:
<223> OTHER INFORMATION: Description of artificial sequence; amino acid
      sequence of 6E4HV0LV0_VH

<400> SEQUENCE: 1

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Glu Ile Asn Pro Arg Asn Gly Gly Thr Asn Asn Asn Glu Asn Phe
50                  55                  60

Lys Arg Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Asp Pro Phe Ala Tyr Trp Gly Gln Gly Thr
                100                 105                 110

Leu Val Thr Val Ser Ser
                115

<210> SEQ ID NO 2
<211> LENGTH: 113
<212> TYPE: PRT
<213> ORGANISM: Artificial
<220> FEATURE:
<223> OTHER INFORMATION: Description of artificial sequence; amino acid
      sequence of 6E4HV0LV0_VL

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Tyr Thr Phe Gly Gln Gly Thr Lys Leu Glu Ile
                100                 105                 110

Lys

<210> SEQ ID NO 3
<211> LENGTH: 5
<212> TYPE: PRT
<213> ORGANISM: Artificial
<220> FEATURE:
<223> OTHER INFORMATION: Description of artificial sequence; amino acid
      sequence of 6E4HV0LV0_H_CDR1

<400> SEQUENCE: 3

Ser Tyr Trp Met His
```

-continued

```
<210> SEQ ID NO 4
<211> LENGTH: 17
<212> TYPE: PRT
<213> ORGANISM: Artificial
<220> FEATURE:
<223> OTHER INFORMATION: Description of artificial sequence; amino acid
      sequence of 6E4HV0LV0_H_CDR2

<400> SEQUENCE: 4

Glu Ile Asn Pro Arg Asn Gly Gly Thr Asn Asn Asn Glu Asn Phe Lys
1               5                   10                  15
Arg

<210> SEQ ID NO 5
<211> LENGTH: 9
<212> TYPE: PRT
<213> ORGANISM: Artificial
<220> FEATURE:
<223> OTHER INFORMATION: Description of artificial sequence; amino acid
      sequence of 6E4HV0LV0_H_CDR3

<400> SEQUENCE: 5

Asp Gly Asn Tyr Asp Pro Phe Ala Tyr
1               5

<210> SEQ ID NO 6
<211> LENGTH: 16
<212> TYPE: PRT
<213> ORGANISM: Artificial
<220> FEATURE:
<223> OTHER INFORMATION: Description of artificial sequence; amino acid
      sequence of 6E4HV0LV0_L_CDR1

<400> SEQUENCE: 6

Arg Ser Ser Gln Ser Leu Val His Ser Asn Gly Asn Thr Tyr Leu His
1               5                   10                  15

<210> SEQ ID NO 7
<211> LENGTH: 7
<212> TYPE: PRT
<213> ORGANISM: Artificial
<220> FEATURE:
<223> OTHER INFORMATION: Description of artificial sequence; amino acid
      sequence of 6E4HV0LV0_L_CDR2

<400> SEQUENCE: 7

Lys Val Ser Asn Arg Phe Ser
1               5

<210> SEQ ID NO 8
<211> LENGTH: 10
<212> TYPE: PRT
<213> ORGANISM: Artificial
<220> FEATURE:
<223> OTHER INFORMATION: Description of artificial sequence; amino acid
      sequence of 6E4HV0LV0_L_CDR3

<400> SEQUENCE: 8

Ser Gln Ser Thr His Val Pro Pro Tyr Thr
1               5                   10
```

METHOD FOR MEASURING TOXICITY OF HUMAN CSF

RELATED APPLICATIONS

This application is a National Stage of International Application No. PCT/JP2015/061765 filed Apr. 16, 2015, claiming priority based on U.S. Provisional Applications No. 61/980,206 filed Apr. 16, 2014, the contents of all of which are incorporated herein by reference in their entirety.

TECHNICAL FIELD

The present invention relates to a method for measuring the toxicity of human cerebrospinal fluid (hereinafter, referred to as "CSF"), a method for determining Alzheimer's disease, a method for measuring the medicinal effect of an agent for preventing and/or treating Alzheimer's disease, a method for determining the sensitivity of a subject to an agent for preventing and/or treating Alzheimer's disease, a method for screening an agent for preventing and/or treating Alzheimer's disease, and a method for creating an Alzheimer's disease-like model animal.

BACKGROUND ART

Soluble aggregates (oligomers) of amyloid β (amyloid beta; hereinafter, also referred to as "Aβ") have been suggested as the primary pathogenic cause of Alzheimer's disease (hereinafter, also referred to as "AD") (Non Patent Literature 1).

Although it is commonly recognized that the Aβ oligomer in the CSF represents an important clinical biomarker for measuring the medicinal effect of an agent targeting Aβ such as an anti-Aβ antibody, detailed attributes (such as structure, size, and origin) of the Aβ oligomer actually eliciting pathology in AD patients remain elusive (Non Patent Literature 2). Some way of measuring such pathological Aβ oligomers is thus desired.

A method that biochemically measures Aβ oligomer levels in human CSF, and a bioassay that measures the bioactivity of human CSF are currently available as methods for measuring Aβ oligomer in human CSF. Assay systems based on immunoassay have been studied as a method for biochemically measuring Aβ oligomer levels. However, because of the considerably low Aβ oligomer levels in CSF, there is hardly any report that had success in such measurement. The bioassay is available as an in vitro test and an in vivo test, as described below.

There is a report of an in vitro test in which cell death, synaptic degeneration, and other changes occurred in cultured nerve cells acted upon by a high concentration (nM order) of artificial Aβ oligomer (Non Patent Literature 3).

There are also reports that nerve cells are damaged when cell lines from nerve cells are acted upon by CSF collected from an AD patient (hereinafter, referred to as "AD patient CSF") (Non Patent Literatures 4 and 5).

There is also a report that electrostimulation of a mouse hippocampus slice after exposure to an artificial Aβ oligomer suppresses long-term potentiation (hereinafter, "LTP"), which is a phenomenon associated with brain's memory formation, in the slice (Non Patent Literature 6).

As to the in vivo test, there is a report in which electrostimulation after administration of AD patient CSF in the rat cerebral ventricle suppressed LTP in the rat brain (Non Patent Literature 7).

There are also reports that the learning behavior of rats or mice is obstructed when an artificial Aβ oligomer or oligomers extracted from cultured cells or brain tissue are administered into the rat or mouse cerebral ventricles (Non Patent Literatures 8 and 9). However, there is no report of administering AD patient CSF to rodents, and measuring the animals for the presence or absence of any resulting learning behavior impairment.

While bioassays of Aβ oligomers in AD patient CSF are available as described above, there is no established bioassay that can quickly and efficiently evaluate human CSF bioactivity, namely human CSF toxicity, with small amounts of CSF.

RELATED ART

Non-Patent Document

[NPL 1] Nat. Neurosci., 2012, vol. 15, p. 349
[NPL 2] Nat. Med., 2010, vol. 16, p. 1218
[NPL 3] Neuron., 2010, vol. 66, p. 739
[NPL 4] Cell. Stress. Chaperones., 2010, vol. 15, p. 115
[NPL 5] Cell. Biochem. Funct., 2009, vol. 27, p. 395
[NPL 6] Brain. Res., 2009, vol. 1269, p. 176
[NPL 7] J. Neurosci., 2008, vol. 28, p. 4231
[NPL 8] PLoS. One., 2012, vol. 7, e29940
[NPL 9] Neurobiol. Aging., 2011, vol. 32, p. 1784

SUMMARY OF INVENTION

Problems to be Solved by the Invention

Accordingly, an object of the present invention is to provide a method that can quickly and efficiently evaluate the toxicity of human CSF with small amounts of human CSF.

Another object of the present invention is to provide a method for quickly and efficiently determining Alzheimer's disease with small amount of human CSF.

Another object of the present invention is to provide a method for quickly and efficiently measuring the medicinal effect of an agent for preventing and/or treating Alzheimer's disease with small amounts of human CSF.

Another object of the present invention is to provide a method for quickly and efficiently measuring the sensitivity of a subject to an agent for preventing and/or treating Alzheimer's disease with small amounts of human CSF.

Another object of the present invention is to provide a method for quickly and efficiently screening an agent for preventing and/or treating Alzheimer's disease with small amounts of human CSF.

Another object of the present invention is to provide a method for quickly and efficiently creating an Alzheimer's disease-like model animal with small amounts of human CSF.

Means for Solving the Problems

The present inventors conducted extensive studies and found that the foregoing problems can be solved by administering human CSF into the cerebral ventricle of a rodent, and evaluating the cognitive function of the rodent by using a behavioral pharmacological technique, thereby completing the present invention.

Namely, the present invention is as follows.

1. A method for measuring the toxicity of human cerebrospinal fluid (hereinafter, referred to as "CSF"), comprising
   administering human CSF into the cerebral ventricle of a rodent, and
   evaluating the cognitive function of the rodent by using a behavioral pharmacological technique.
2. The method according to above 1, wherein the cognitive function evaluation is evaluation of the short-term memory of the rodent.
3. The method according to above 1 or 2, wherein the behavioral pharmacological technique is a Y-maze test.
4. The method according to any one of above 1 to 3, wherein dosage of the human CSF administered into the cerebral ventricle of the rodent is 5 µl or more.
5. The method according to any one of above 1 to 4, wherein the rodent is a mouse.
6. A method for determining Alzheimer's disease, comprising
   administering human CSF into the cerebral ventricle of a rodent, and
   evaluating the cognitive function of the rodent by using a behavioral pharmacological technique.
7. The method according to above 6, wherein the cognitive function evaluation is evaluation of the short-term memory of the rodent.
8. The method according to above 6 or 7, wherein the behavioral pharmacological technique is a Y-maze test.
9. The method according to any one of above 6 to 8, wherein dosage of the human CSF administered into the cerebral ventricle of the rodent is 5 µl or more.
10. The method according to any one of above 6 to 9, comprising comparing the cognitive function of the rodent administered with a control into the cerebral ventricle and the cognitive function of the rodent administered with the human CSF into the cerebral ventricle.
11. The method according to any one of above 6 to 10, wherein the rodent is a mouse.
12. A method for measuring the medicinal effect of an agent for preventing and/or treating Alzheimer's disease, comprising
    administering human CSF into the cerebral ventricle of a rodent, and
    evaluating the cognitive function of the rodent by using a behavioral pharmacological technique.
13. The method according to above 12, wherein the cognitive function evaluation is evaluation of the short-term memory of the rodent.
14. The method according to above 12 or 13, wherein the behavioral pharmacological technique is a Y-maze test.
15. The method according to any one of above 12 to 14, wherein dosage of the human CSF administered into the cerebral ventricle of the rodent is 5 µl or more.
16. The method according to any one of above 12 to 15, comprising
    (1) collecting human CSF from a subject starting or continuously undergoing administration of the agent for preventing and/or treating Alzheimer's disease before and after the administration of the agent; and
    (2) administering each of the human CSFs of before and after the administration of the agent collected in the step (1) into the cerebral ventricle of a rodent and comparing the cognitive function of the rodent.
17. The method according to any one of above 12 to 16, wherein the agent for preventing and/or treating Alzheimers disease is an anti-amyloid β (amyloid beta, hereinafter referred to as "Aβ") oligomer antibody.
18. The method according to any one of above 12 to 17, wherein the agent for preventing and/or treating Alzheimer's disease is an antibody selected from the following (a) and (b):
    (a) a monoclonal antibody in which complementarity determining region (hereinafter, referred to as "CDR") 1, CDR2, and CDR3 of the heavy chain variable region (hereinafter, referred to as "VH") of the antibody comprise the amino acid sequences represented by SEQ ID NOS: 3, 4, and 5, respectively, and CDR1, CDR2, and CDR3 of the light chain variable region (hereinafter, referred to as "L") of the antibody comprise the amino acid sequences represented by SEQ ID NOS: 6, 7, and 8, respectively; and
    (b) a monoclonal antibody in which the VH of the antibody comprises the amino acid sequence represented by SEQ ID NO: 1, and the VL comprises the amino acid sequence represented by SEQ ID NO: 2.
19. The method according to any one of above 12 to 18, wherein the rodent is a mouse.

Effects of the Invention

According to the present invention, by administering a human CSF into the cerebral ventricle of a rodent, and evaluating the cognitive function of the rodent by using a behavioral pharmacological technique, a method for quickly and efficiently evaluating the toxicity of human CSF with small amounts of human CSF, a method for quickly and efficiently determining Alzheimers disease with small amounts of human CSF, a method for quickly and efficiently measuring the medicinal effect of an agent for preventing and/or treating Alzheimer's disease with small amounts of human CSF, a method for quickly and efficiently predicting the sensitivity of a subject to an agent for preventing and/or treating Alzheimer's disease with small amounts of human CSF, a method for quickly and efficiently screening an agent for preventing and/or treating Alzheimer's disease with small amounts of human CSF, and a method for quickly and efficiently creating an Alzheimer's disease-like model animal with small amounts of human CSF are provided.

BRIEF DESCRIPTION OF THE DRAWINGS

FIG. 6 (a) and FIG. 6 (b) are diagrams explaining a Y-maze test apparatus.

EMBODIMENTS FOR CARRYING OUT THE INVENTION

Hereinafter, the present invention will be described in detail.

[Human CSF Toxicity Measurement Method]

At first, a method for measuring the toxicity of human CSF is described below. The method comprises administering a human CSF into the cerebral ventricle of a rodent, and evaluating the cognitive function of the rodent by using a behavioral pharmacological technique.

The human CSF is not particularly limited, as long as it is CSF collected from humans. For example, the human CSF may be a commercially available human CSF, human CSF collected by a physician from a subject, or any other CSFs, including a CSF immediately after being collected from humans, and a collected human CSF that is cryopreserved and thawed as necessary for use.

Examples of the rodent include mice, rats, and hamsters, of which mice are preferred.

When human CSF is administrated into intraventricular, human CSF may be administrated into the left cerebral ventricle, the right cerebral ventricle or both cerebral ventricles. As an administration method of human CSF, a conventional method of administrating an agent or the like into the cerebral ventricles can be used (Scientific Reports, 2014, vol. 4, 6777).

A dosage of human CSF administered into the cerebral ventricle is, for example, preferably 5 μl or more, more preferably 10 μl for mice. After one hour from administrating 5 μl or greater of human CSF into mouse intraventricular, human CSF toxicity is able to be measured. A dosage of human CSF administered into the cerebral ventricles of rodents other than mice may be set according to the method described in Example 1 of this application.

In the present invention, behavioral pharmacological techniques may be used for the evaluation of rodent's cognitive function. As a cognitive function, functions include short-term memory, kinesthetic memory, associative learning, horror learning, latent learning, visual perception memory, long-term memory, spatial work, reference memory, spatial learning, spatial memory, working memory, and the like. Examples of evaluation methods of rodent's cognitive function using behavioral pharmacological techniques include known tests such as a Y-maze test, a T-maze test, a rotarod test, a contextual fear conditioning test, a water-finding test, a novel object finding test, a passive avoidance test, a radial maze test, a Morris water maze test, a delayed matching and non-matching to sample test, and the like.

In the present invention, it is preferable to evaluate the short-term memory as the rodent's cognitive function, preferably by using a Y-maze test as a specific method.

The methodology of such a Y-maze test is described in Alkam et al., [Behav. Brain Res.), Vol. 180, p. 139 (2007)].

Figure 6:
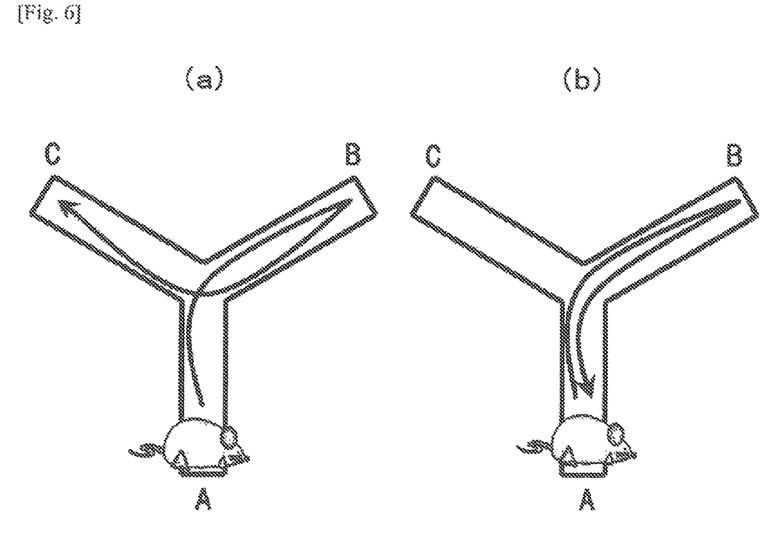

Specifically, a Y-maze test apparatus is set up as shown in FIG. 6 (a) and FIG. 6 (b). The Y-maze test apparatus is constructed from, for example, three arms A, B, and C each forming black acryl walls, and these are joined to each other at 120-degree angle. A rodent is allowed to freely move inside the three arms A, B, and C.

A normal rodent has the tendency to successively enter the three arms A, B, and C, as indicated by arrow in FIG. 6(a). Such a behavior manifested as successive entry into different three arms is defined as a spontaneous alternation behavior. A rodent with cognitive deficits shows a tendency to move back and forth between two arms, as indicated by arrow in FIG. 6(b).

In other words, the percentage of spontaneous alternation behavior over a certain time period is smaller in a rodent with cognitive deficits than in a normal rodent.

The percentage of spontaneous alternation behavior over a certain time period is defined as spontaneous alternation (%), and may be calculated according to the equation (1) below. The presence or absence of cognitive function impairment can be determined on the basis of spontaneous alternation as described above, and this value can be used as the basis of human CSF toxicity measurement, specifically the determination of the presence or absence of human CSF toxicity.

The following equation (1) is used to calculate spontaneous alternation (%). Formula (2) represents a method for counting spontaneous alternation behaviors.

$$\text{Spontaneous alternation (\%)} = \{\text{number of spontaneous alternation behaviors}/(\text{total number of entry into arms}-2)\} \times 100(\%) \qquad \text{Formula (1)}$$

The following describes the result of a mouse Y-maze test and the spontaneous alternation (%) calculated from the equation (1). The result of a mouse Y-maze test conducted with the apparatus shown in FIG. 6 (a) and FIG. 6 (b) is described first.

[Math 1]

Formula (2)

In the Formula (2), the total number of entry into the arms A, B, and C is ten, and five out of the ten movements represents a spontaneous alternation behavior, as indicated by upper and lower brackets. It follows from the equation (1) that the spontaneous alternation (%) is $\{5/(10-2)\} \times 100$ (%)=62.5%.

For the determination of whether the human CSF administered to a mouse has toxicity, spontaneous alternation (%) is compared between a rodent that had intraventricular administration of a human CSF, and a rodent that had intraventricular administration of a control such as physiological saline. The human CSF can be determined as having toxicity when the human CSF-administered rodent has a lower spontaneous alternation (%) than the control.

The extent of decrease in spontaneous alternation (%) may be measured as, for example, a statistically significant decrease. By "statistically significant", it means, for example, the difference of the spontaneous alternation (%) values obtained according to the method described in Example 1 of this application is significant for $p<0.05$ as measured by Dunnett's test performed for a rodent that had intraventricular administration of a control such as physiological saline and a rodent that had intraventricular administration of the human CSF.

The extent of decrease in spontaneous alternation (%) may be a decrease by 3% or more, 5% or more, 7% or more, 10% or more, or 20% or more.

[Alzheimer's Disease Determination Method]

Next, a method for determining Alzheimer's disease of the present invention is described below. The method comprises administering human CSF into the cerebral ventricle of a rodent, and evaluating the cognitive function of the rodent by using a behavioral pharmacological technique.

The human CSF is not particularly limited, as long as it is CSF collected from humans, as above. Examples of the rodent include mice, rats, and hamsters, and mice are preferred, as noted above.

The administration method of the human CSF into the cerebral ventricles is the same as above.

A dosage of human CSF administered into the cerebral ventricle is, for example, 5 µl or more, preferably 10 µl for mice. A dosage of the human CSF administered into the cerebral ventricles of other rodents may be set according to the method described in Example 1 of this application.

In the method for determining Alzheimer's disease of the present invention, the rodent's cognitive function is evaluated by using a behavioral pharmacological technique, and various known tests may be used as such techniques, as exemplified above.

In the method for determining Alzheimer's disease of the present invention, it is preferable to evaluate the rodent's short-term memory, preferably by using a Y-maze test which can evaluate rodent's short-term memory.

The Y-maze test, the spontaneous alternation behavior, the spontaneous alternation (%), and the calculation methods are as described above.

For accurate determination, the method for determining Alzheimer's disease of the present invention preferably comprises comparing spontaneous alternation (%) between a rodent that had intraventricular administration of a control (for example, physiological saline) and a rodent that had intraventricular administration of human CSF.

In assessments made by the present inventors, a patient can be determined as having a high likelihood of having Alzheimer's disease when a rodent that had intraventricular administration of the human CSF collected from the patient has a lower spontaneous alternation (%) than the rodent that had intraventricular administration of a control (for example, physiological saline).

The extent of decrease in spontaneous alternation (%) may be measured as, for example, a statistically significant decrease. By "statistically significant", it means, for example, the difference of the spontaneous alternation (%) values obtained according to the method described in Example 1 of this application is significant for $p<0.05$ as measured by Dunnett's test performed for a rodent that had intraventricular administration of a control such as physiological saline and a rodent that had intraventricular administration of the human CSF.

The extent of decrease in spontaneous alternation (%) may be a decrease by 3% or more, 5% or more, 7% or more, 10% or more, or 20% or more.

The determination method of the present invention also may be used to determine prodromal Alzheimer's disease.

[Method for Measuring the Medicinal Effect of Agent for Preventing and/or Treating Alzheimer's Disease]

Next, a method for measuring the medicinal effect of an agent for preventing and/or treating Alzheimer's disease of the present invention is described below. The method comprises administering human CSF into the cerebral ventricle of a rodent, and evaluating the cognitive function of the rodent by using a behavioral pharmacological technique.

The human CSF is not particularly limited, as long as it is CSF collected from humans, as above. Examples of the rodent include mice, rats, and hamsters, and mice are preferred, as noted above.

The administration method of the human CSF into the cerebral ventricles is the same as above.

The dosage of human CSF administered into the cerebral ventricle is, for example, 5 µl or more, more preferably 10 µl for mice. The dosage of the human CSF administered into the cerebral ventricles of other rodents may be set according to the method described in Example 1 of this application.

In the method for measuring the medicinal effect of an agent for preventing and/or treating Alzheimer's disease of the present invention, the rodent's cognitive function is evaluated by using a behavioral pharmacological technique, and various known tests may be used as such techniques, as exemplified above.

In the method for measuring the medicinal effect of an agent for preventing and/or treating Alzheimer's disease of the present invention, it is preferable to evaluate the rodent's short-term memory, preferably by using a Y-maze test which can evaluate rodent's short-term memory.

The Y-maze test, the spontaneous alternation behavior, the spontaneous alternation (%), and the calculation methods are as described above.

For medicinal effect determination, the method for measuring the medicinal effect of an agent for preventing and/or treating Alzheimer's disease of the present invention preferably comprises the following steps (1) and (2).

(1) collecting human CSF from a subject starting or continuously undergoing administration of the agent for preventing and/or treating Alzheimer's disease before and after the administration of the agent; and (2) administering each of the human CSFs of before and after the administration of the agent collected in the step (1) into the cerebral ventricle of a rodent and comparing the cognitive function of the rodent.

In step (2), (A) the spontaneous alternation (%) of the rodent that had intraventricular administration of the human CSF collected before the administration of the agent, and (B) the spontaneous alternation (%) of the rodent that had intraventricular administration of the human CSF collected after the administration of the agent are compared for the human CSFs collected in step (1).

The presence or absence of medicinal effect can thus be measured with this technique. As used herein, "after the administration of the agent" may be after single or multiple administration of the agent following the previous collection of the human CSF.

The medicinal effect can be confirmed, for example, upon finding that the spontaneous alternation (%) (B) is higher than the spontaneous alternation (%) (A). The extent of increase of spontaneous alternation (%) may be measured by, for example, statistical significance. By "statistically significant", it means, for example, the difference between the two groups is significant for $p<0.05$ in a Dunnett's test.

In the case of mice, for example, the agent may be considered effective when the percentage improvement (%) of the spontaneous alternation calculated according to equation 3 described in Example 6 of this application is 40% or more, 60% or more, 80% or more, or 100%.

The agent for preventing and/or treating Alzheimer's disease of the present invention include all agents that can serve as inhibitory factors of Alzheimer's disease, including agents for the prevention and amelioration of Alzheimer's disease.

Examples include known acetylcholine esterase inhibitors, NMDA receptor antagonists, anti-Aβ oligomer antibodies, and amyloid β vaccines. Preferred as the agent for preventing and/or treating Alzheimer's disease are anti-Aβ oligomer antibodies.

In particular, the anti-Aβ oligomer antibody is one selected from the following (a) and (b):

(a) a monoclonal antibody in which complementarity determining region (hereinafter, referred to as "CDR") 1, CDR2, and CDR3 of the heavy chain variable region (hereinafter, referred to as "VH") of the antibody comprise the amino acid sequences represented by SEQ ID NOS: 3, 4, and 5, respectively, and CDR1, CDR2, and CDR3 of the light chain variable region (hereinafter, referred to as "VL") of the antibody comprise the amino acid sequences represented by SEQ ID NOS: 6, 7, and 8, respectively; and (b) a monoclonal antibody in which the VH of the antibody comprises the amino acid sequence represented by SEQ ID NO: 1, and the VL of the antibody comprises the amino acid sequence represented by SEQ ID NO: 2.

These monoclonal antibodies, and producing processes of these antibodies are disclosed in WO2009/099176, and WO2011/016567.

The medicinal effect of the agent may represent a therapeutic effect on an agent-administered subject as measured at the time of the CSF collection, or a therapeutic effect expected to occur in a subject in the future.

The present invention also can measure the medicinal effect over a time course in a subject continuously undergoing administration of the agent for preventing and/or treating Alzheimer's disease. For the time-course medicinal effect measurement, it is preferable to collect CSF from the subject at multiple time points in the agent administration schedule.

The method of the present invention also may be used to measure the medicinal effect of an agent for preventing and/or treating prodromal Alzheimer's disease.

[Method for Determining Sensitivity to Agent for Preventing and/or Treating Alzheimer's Disease]

The present invention is also concerned with a method for determining the sensitivity of a subject Alzheimer's disease patient to an agent for preventing and/or treating Alzheimer's disease. The method comprises administering human CSF into the cerebral ventricle of a rodent, and evaluating the cognitive function of the rodent by using a behavioral pharmacological technique.

Preferably, the subject is an Alzheimer's disease patient who has never been administered with the agent.

The human CSF is not particularly limited, as long as it is a CSF collected from humans, as above. Examples of the rodent include mice, rats, and hamsters, and mice are preferred, as noted above.

The administration method of the human CSF into the cerebral ventricles is the same as above.

A dosage of human CSF into the cerebral ventricle is, for example, 5 µl or more, more preferably 10 µl for mice. A dosage of the human CSF administered into the cerebral ventricles of other rodents may be set according to the method described in Example 1 of this application.

In the method for determining the sensitivity of a subject to an agent for preventing and/or treating Alzheimer's disease of the present invention, the rodent's cognitive function is evaluated by using a behavioral pharmacological technique, and various known tests may be used as such techniques, as exemplified above.

In the method for determining the sensitivity of a subject to an agent for preventing and/or treating Alzheimers disease of the present invention, it is preferable to evaluate the rodent's short-term memory, preferably by using a Y-maze test which can evaluate rodent's short-term memory.

The Y-maze test, the spontaneous alternation behavior, the spontaneous alternation (%), and the calculation methods are as described above. The presence or absence of the sensitivity of an Alzheimer's disease patient to the agent may be confirmed by comparing the spontaneous alteration of a rodent when the agent and AD patient CSF are administrated into the rodent with the spontaneous alteration of a rodent when a control and AD patient CSF are administrated into the rodent. The agent and AD patient CSF or the control and AD patient CSF may be administrated in a mixed state beforehand, or may be administrated separately. Administration interval and order of administration are not limited when administrating separately. Administration area or administration method of the test agent is not limited, and for example, intravenous administration or administration into cerebral ventricle is exemplified. The presence or absence of the sensitivity of an Alzheimer's disease patient to the agent may be confirmed, for example, according to the methods described in Examples 4 and 5 of this application.

Sensitivity to the agent means that the spontaneous alteration of a rodent when the agent and AD patient CSF are administrated into the rodent increases compared to the spontaneous alteration of a rodent when the control and AD patient CSF are administrated into the rodent. For example, it is exemplified that the agent i.v.-AD CSF administered group has a higher spontaneous alternation than the Human IgG4 i.v.-AD CSF administered group according to the method described in Example 4 of this application.

Sensitivity to the agent also can be confirmed upon finding that the agent-AD CSF administered group has a higher spontaneous alternation than the vehicle-AD CSF administered group according to the method described in Example 5 of this application.

The extent of increase of spontaneous alternation (%) may be measured by, for example, statistical significance. By "statistically significant", it means, for example, the difference between the two groups is significant for $p<0.05$ in a Dunnett's test.

In the case of mice, for example, sensitivity to the agent may be considered present when the percentage improvement (%) of the spontaneous alternation calculated according to Formula (3) described in Example 6 of this application is 40% or more, 60% or more, 80% or more, or 100%.

The invention concerning the agent for preventing and/or treating Alzheimer's disease is described above.

The method of the present invention also may be used to measure the sensitivity of a subject to an agent for preventing and/or treating prodromal Alzheimer's disease.

[Method for Creating Alzheimer's Disease-Like Model Animal]

The present invention is also concerned with a method for creating an Alzheimer's disease-like model animal. The method comprises administering human CSF into the cerebral ventricle of a rodent, and evaluating the cognitive function of the rodent by using a behavioral pharmacological technique.

The human CSF is not particularly limited, as long as it is a CSF collected from humans, as above. Examples of the rodent include mice, rats, and hamsters, and mice are preferred, as noted above.

The administration method of the human CSF into the cerebral ventricles is the same as above.

A dosage of human CSF administered into the cerebral ventricle is, for example, 5 μl or more, preferably 10 μl for mice. A dosage of the human CSF administered into the cerebral ventricles of other rodents may be set according to the method described in Example 1 of this application.

In the method for creating an Alzheimer's disease-like model animal of the present invention, the rodent's cognitive function is evaluated by using a behavioral pharmacological technique, and various known tests may be used as such techniques, as exemplified above.

In the method for creating an Alzheimer's disease-like model animal of the present invention, it is preferable to evaluate the rodent's short-term memory, preferably by using a Y-maze test which can evaluate rodent's short-term memory.

The Y-maze test, the spontaneous alternation behavior, the spontaneous alternation (%), and the calculation methods are as described above.

In the method for creating an Alzheimer's disease-like model animal of the present invention, a rodent that had intraventricular administration of the human CSF can be said as an Alzheimer's disease-like model animal, for example, when the rodent that had intraventricular administration of the human CSF has a lower spontaneous alternation (%) as compared to a rodent that had intraventricular administration of a control such as physiological saline.

The extent of decrease in spontaneous alternation (%) may be measured as, for example, a statistically significant decrease. By "statistically significant", it means, for example, the difference of the spontaneous alternation (%) values obtained according to the method described in Example 1 of this application is significant for $p<0.05$ as measured by Dunnett's test performed for a rodent that had intraventricular administration of a control such as physiological saline and a rodent that had intraventricular administration of the human CSF.

The extent of decrease in spontaneous alternation (%) may be a decrease by 3% or more, 5% or more, 7% or more, 10% or more, or 20% or more.

[Method for Screening Agent for Preventing and/or Treating Alzheimer's Disease]

The present invention is also concerned with a method for screening an agent for preventing and/or treating Alzheimer's disease. The method comprises steps of administering human CSF into cerebral ventricle of a rodent, and evaluating cognitive function of rodent by using a behavioral pharmacological technique. In the method, the model animal obtained by using the method for creating an Alzheimer's disease-like model animal can be used.

The human CSF is not particularly limited, as long as it is CSF collected from humans, as described above. Examples of the rodent include mice, rats, and hamsters, of which mice are preferred, as described above.

The administration method of the human CSF into the cerebral ventricles is the same as above.

A dosage of human CSF administered into the cerebral ventricle is, for example, 5 μl or more, more preferably 10 μl for mice. A dosage of the human CSF administered into the cerebral ventricles of other rodents may be set according to the method described in Example 1 of this application.

In the method for screening an agent for preventing and/or treating Alzheimer's disease of the present, the cognitive function of the rodent is evaluated by using a behavioral pharmacological technique, and various known tests may be used as such techniques, as exemplified above.

In the method for screening an agent for preventing and/or treating Alzheimer's disease of the present, it is preferable to evaluate the rodent's short-term memory, preferably by using a Y-maze test which can evaluate rodent's short-term memory.

The Y-maze test, the spontaneous alternation behavior, the spontaneous alternation (%), and the calculation methods are as described above.

As the method for screening an agent for preventing and/or treating Alzheimer's disease of the present invention, it is exemplified that in case where the spontaneous alteration of a rodent when a test agent and AD patient CSF are administrated into the rodent increases compared to the spontaneous alteration of a rodent when a control and AD patient CSF are administrated into the rodent, the test agent is selected as candidate of the agent for preventing and/or treating Alzheimer's disease. The test agent and AD patient CSF or the control and AD patient CSF may be administrated in a mixed state beforehand, or may be administrated separately. Administration interval and order of administration are not limited when administrating separately. Administration area or administration method of the test agent is not limited, and for example, intravenous administration or administration into cerebral ventricle is exemplified. As a specific example, the method for screening an agent for preventing and/or treating Alzheimer's disease of the present invention includes selecting test agent as a candidate agent for preventing and/or treating Alzheimer's disease when a test agent i.v.-AD CSF administered group has a higher spontaneous alternation than a human IgG4 i.v.-AD CSF administered group as measured according to the method described in Example 4 of this application.

As another example, a test agent may be selected as an agent for preventing and/or treating Alzheimer's disease when a test agent-AD CSF administered group has a higher spontaneous alternation than a vehicle-AD CSF administered group as measured according to the method described in Example 5 of this application.

The extent of increase of spontaneous alternation (%) may be measured by, for example, statistical significance. By "statistically significant", it means, for example, the difference between the two groups is significant for $p<0.05$ in a Dunnett's test.

In the method for screening an agent for preventing and/or treating Alzheimer's disease of the present invention, a test agent may be selected as an agent for preventing and/or treating Alzheimer's disease when the test agent improves the spontaneous alternation 40% or more, 60% or more, 80% or more, or 100% in the case of for example, mice, as calculated according to Formula (3) described in Example 6 of this application.

The test agents used in the present invention are not particularly limited, and may be, for example, small molecules, proteins (including antibodies), and peptides.

The method of the present invention also may be used for screening of an agent for preventing and/or treating prodromal Alzheimer's disease.

EXAMPLES

The present invention is described below in greater detail using Examples. Note, however, that the present invention is not limited by the following Examples.

Example 1

Measurement of Mouse Cognitive Function Impairment by AD Patient CSF

The cognitive function of mice administered with AD patient CSF was measured by Y-maze test. Y-maze test was performed according to the method described in Alkam et al., [Behav. Brain Res.), Vol. 180, p. 139 (2007)].

AD patient CSF (Precision Med) was administered into the cerebral ventricles of ICR mice (male, Japan SLC) in a 1, 3, 5, or 10 µl dose under isoflurane anesthesia. The CSF was administered into the left cerebral ventricle for the 1, 3, and 5 µl administration, and into the left and right cerebral ventricles for the 10 µl administration, 5 µl to each ventricle.

As a negative control, physiological saline (hereinafter, "Sham"; Otsuka Pharmaceutical Factory Co., Ltd.) was administered in the maximum dose 10 µl into the mouse cerebral ventricles in the same manner as above.

After 1 hour from the intraventricular administration, each mouse was put in the tip portion of one of the three arms A, B, and C of a Y-maze test apparatus shown in FIG. 6 (a) and FIG. 6 (b) [the arms are each constructed as black acryl walls measuring 25 cm in length, 5 cm in width, and 20 cm in height, and joined to each other at 120-degree angle]. The mouse was then allowed to freely explore the maze for 7 minutes.

Here, an entry to an arm is defined as the state when all four limbs of the mouse were within the arm. The order in which the animal entered the arms was recorded, and spontaneous alternation (%) was determined according to the equation, Formula (1) above. The result is presented in FIG. 1.

Figure 1:
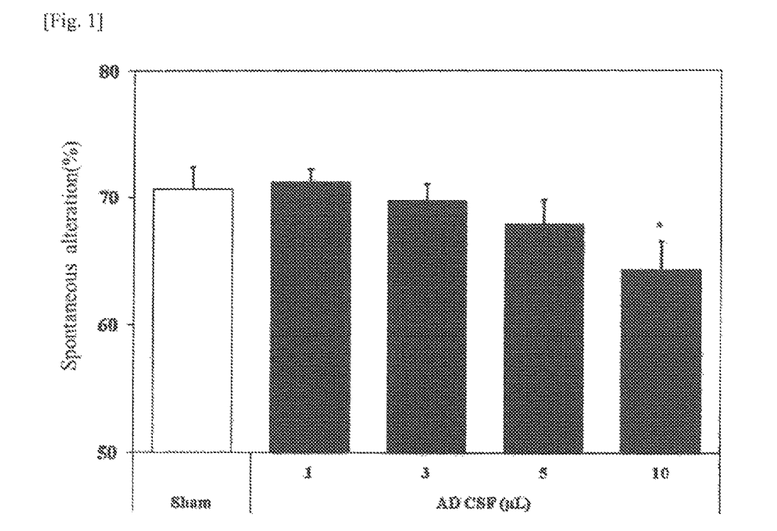
FIG. 1 is a diagram examining the dose response with regard to the effect of AD patient CSF on mouse cognitive function, in which the vertical axis represents spontaneous alternation (%) as an index of cognitive function, and the horizontal axis represents samples administered to mice, along with their dosages (µl). Physiological saline was used as Sham. AD CSF represents AD patient CSF. * represents administered group for p<0.05 (against sham) in Dunnett's test. Experiment was performed with N=12.

As shown in FIG. 1, the spontaneous alternation of the AD patient CSF administered group decreased with increase in the dose of the AD patient CSF. The extent of spontaneous alternation decrease was particularly significant in the 10-µl AD patient CSF administered group as compared to the Sham administered group.

Example 2

Measurement of Mouse Cognitive Function Impairment by Different AD Patient CSFs

The cognitive function of mice administered with AD patient CSFs different from that used in Example 1 was measured by Y-maze test. The AD patient CSFs used in this example are CSFs from two AD patients (both available from Precision Med), and a sample prepared as a mixture of CSFs from 3 patients which is denoted as "Pool" (Cureline), which are different from the CSF used in Example 1.

These AD patient CSFs (10 µl each), or physiological saline (10 Id; hereinafter, "Sham") were administered into the cerebral ventricles of ICR mice under isoflurane anesthesia, and each mouse was tested by Y-maze test in the same manner as in Example 1 to determine spontaneous alternation (%). The results are presented in FIG. 2. The AD patient CSFs and the physiological saline were administrated in 5 µl dose into each of the left and right cerebral ventricles.

Figure 2:
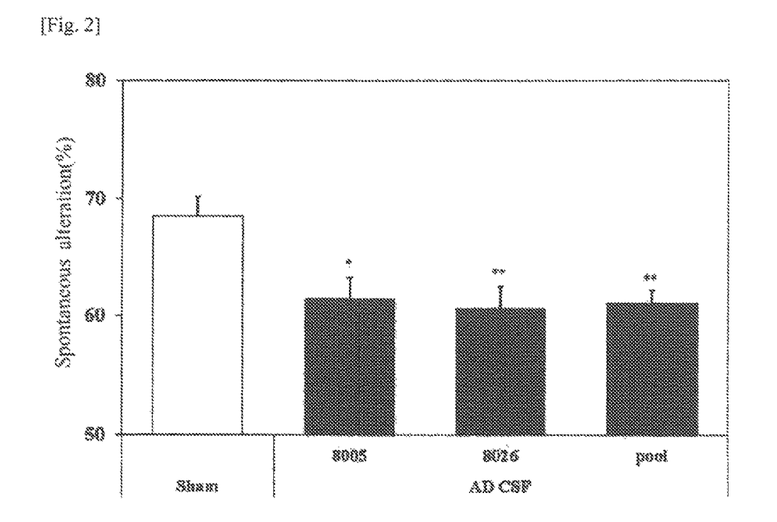
FIG. 2 is a diagram examining the effect of multiple AD patient CSFs on mouse cognitive function, in which the vertical axis represents spontaneous alternation (%) as an index of cognitive function, and the horizontal axis represents samples administered to mice. Physiological saline was used as Sham. AD CSF represents AD patient CSF. The numbers 8005 and 8026 for AD patient CSFs represent patient ID, and Pool represents a sample as a mixture of CSFs from 3 patients. ** represents administered group for p<0.01 (against Sham) in Dunnett's test. * represents administered group for p<0.05 (against Sham). Experiment was performed with N=9.

As shown in FIG. 2, the spontaneous alternation (%) of mice was significantly lower in all AD patient CSF administered groups than in the negative control Sham administered group.

The results observed in Examples 1 and 2 confirmed that the intraventricular administration of 10-µl AD patient CSF significantly lowers the mouse cognitive function compared to the Sham group.

Example 3

Measurement of the Effect of Normal CSF on Mouse Cognitive Function

The cognitive function of mice administered with normal CSFs was measured by Y-maze test. CSFs from three normal individuals (Precision Med) were used as normal CSFs. Physiological saline (hereinafter, "Sham"), and AD patient CSF (Precision Med) were used as negative control and positive control, respectively.

Each sample (10 µl) was administered into the cerebral ventricles of ICR mice under isoflurane anesthesia, and each mouse was tested by Y-maze test in the same manner as in Example 1 to determine spontaneous alternation (%). The results are presented in FIG. 3. Each sample was administrated in 5 µl dose into each the left and right cerebral ventricles of mice.

Figure 3:
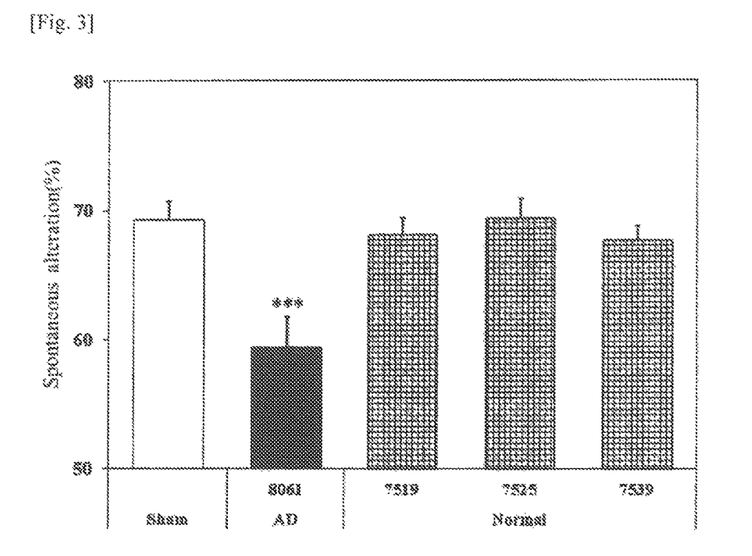
FIG. 3 is a diagram examining the effect of multiple normal CSFs on mouse cognitive function, in which the vertical axis represents spontaneous alternation (%) as an index of cognitive function, and the horizontal axis represents samples administered to mice, and CSF IDs (numbers). Physiological saline was used as Sham. AD represents AD patient CSF. Normal represents normal CSF. *** represents administered group for p<0.001 (against Sham) in Dunnett's test. Experiment was performed with N=8.

As shown in FIG. 3, spontaneous alternation was significantly lower in the positive control AD patient CSF administered group than in the negative control Sham administered group. On the other hand, the normal CSF administered group showed almost the same levels of spontaneous alternation as that of the Sham administered group in all samples.

As demonstrated above, the lowered cognitive function observed in mice administered with AD patient CSF in Examples 1 and 2 was found to be a AD patient CSF-specific phenomenon not observed with the normal CSF. Thus, it was found that administration of AD patient CSF causes decrease in cognitive function of mice and reflects patient's condition.

Example 4

Measurement of the Effect of Anti-Aβ Antibody Intravenous Administration on Mouse Cognitive Function Impairment by AD Patient CSF Next, mice that had intravenous administration of anti-Aβ oligomer antibody were measured for changes in cognitive function after AD patient CSF administration, using a Y-maze test. As the anti-Aβ oligomer antibody, an anti-Aβ oligomer humanized antibody 6E4HV0LV0 was produced according to the method disclosed in WO2011/016567 and known methods, and used in the experiment.

The amino acid sequences of VH and VL of 6E4HV0LV0 are represented by SEQ ID NOS: 1 and 2, respectively. The amino acid sequences of heavy chain CDR1, CDR2, and CDR3 of 6E4HV0LV0 are represented by SEQ ID NOS: 3, 4, and 5, respectively. The amino acid sequences of light chain CDR1, CDR2, and CDR3 are represented by SEQ ID NOS: 6, 7, and 8, respectively.

ICR mice were intravenously administered with 3 mg/kg of human IgG4 (Sigma-Aldrich), or 0.3 mg/kg, 1 mg/kg, or 3 mg/kg of 6E4HV0LV0.

On the next day, 10 µl of physiological saline (hereinafter, "Sham") or the same amount of AD patient CSF (Precision Med) was administered into the cerebral ventricles of the mice under isoflurane anesthesia. Each mouse was then tested by Y-maze test in the same manner as in Example 1 to determine spontaneous alternation (%). The results are presented in FIG. 4. The AD patient CSF and the physiological saline were administered in 5 µl dose into each of the left and right cerebral ventricles.

In the following, mice that had intravenous administration of human IgG4, and intraventricular administration of Sham will be identified by using the notation "human IgG4 i.v.-Sham administered group." Similar notations are used for mice administered with other samples.

Figure 4:
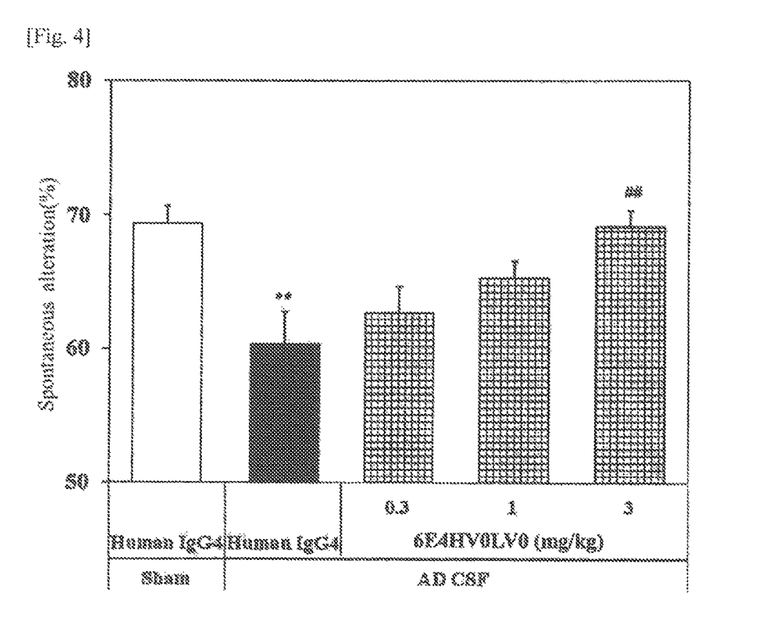
FIG. 4 is a diagram examining the effect of anti-Aβ oligomer humanized antibody (6E4HV0LV0) in intravenous administration on cognitive function impairment by AD patient CSF, in which the vertical axis represents spontaneous alternation (%) as an index of cognitive function. The upper label on the horizontal axis represents the antibody intravenously administered to mice, and antibody dosage (mg/kg). The lower label on the horizontal axis represents samples that had intraventricular administration. Physiological saline was used as Sham. AD CSF represents AD patient CSF. ** represents administered group for p<0.01 (against Human IgG4 i.v.-Sham) in Student's t-test. ## represents administered group for <0.01 (Human IgG4 i.v.-AD CSF) in Dunnett's test. Experiment was performed with N =8.

As shown in FIG. 4, the spontaneous alternation was significantly lower in the Human IgG4 i.v.-AD CSF administered group than in the IgG4 i.v.-Sham administered group.

On the other hand, the spontaneous alternation in the 6E4HV0LV0 i.v.-AD CSF administered group increased with increase in the dose of 6E4HV0LV0. The spontaneous alternation was significantly higher in the 3 mg/kg 6E4HV0LV0 i.v.-AD CSF administered group than in the human IgG4 i.v.-AD CSF administered group, recovering to the same levels as that observed in the human IgG4 i.v.-Sham administered group.

Example 5

Measurement of the Effect of Anti-Aβ Antibody Pretreatment on Mouse Cognitive Function Impairment by AD Patient CSF Example 4 examined the effect of 6E4HV0LV0 intravenous administration. However, in a possible clinical application of the present assay system for the measurement of the medicinal effect of an agent for preventing and/or treating Alzheimer's disease (for example, an agent targeting the Aβ oligomer), CSF is collected from the same patient before and after the agent administration, and the cognitive function of mice administered with these CSFs is measured. That is, the intraventricular administration of the patient's CSF collected after the agent administration involves the agent.

For the purpose of evaluating a sample that more accurately reflects the actual clinical sample, the cognitive function of mice administered with an AD patient CSF pretreated with 6E4HV0LV0 was measured by Y-maze test.

6E4HV0LV0 was added to AD patient CSF (Precision Med) to make the final concentration 1 ng/ml, 10 ng/ml, or 100 ng/ml, and the mixture was incubated at room temperature for about 1 hour.

Artificial cerebrospinal fluid [artificial spinal fluid (Otsuka Pharmaceutical Co., Ltd.) supplemented with 0.02 w/v % human serum albumin (Sigma-Aldrich)](hereinafter, "vehicle") was added to AD patient CSF or physiological saline (hereinafter, "Sham"), and the mixture was incubated at room temperature. The prepared sample was preserved at −80° C., and used for the experiment after being thawed at room temperature on the day of the Y-maze testing.

The sample (10 µl each) was administered into the cerebral ventricles of ICR mice under isoflurane anesthesia, and each mouse was tested by Y-maze test in the same manner as in Example 1 to determine spontaneous alternation (%).

Figure 5:
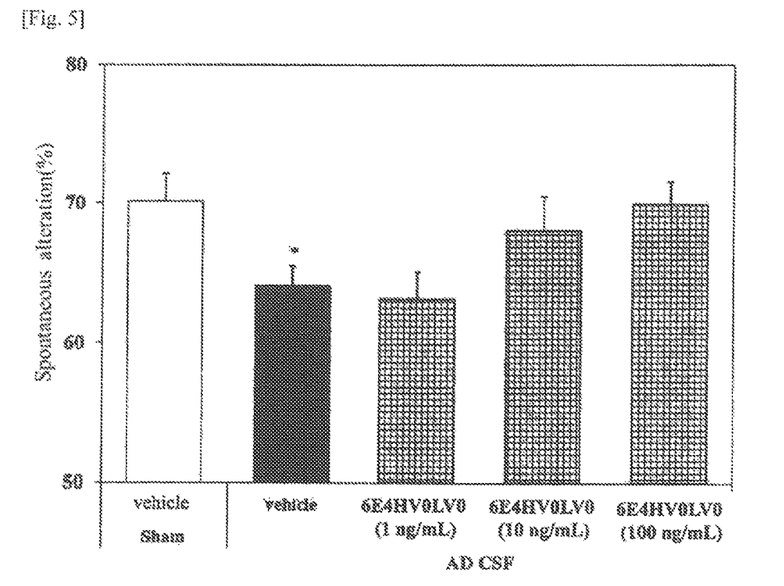
FIG. 5 is a diagram examining the effect of anti-Aβ oligomer antibody (6E4HV0LV0) in pretreatment on cognitive function impairment by AD patient CSF, in which the vertical axis represents spontaneous alternation (%) as an index of cognitive function, and the horizontal axis represents samples administered to mice, and sample concentration (ng/ml). Physiological saline was used as Sham. Artificial cerebrospinal fluid was used as Vehicle. AD CSF represents AD patient CSF. * represents administered group for p<0.05 (against vehicle-Sham) in Student's t-test. Experiment was performed with N=8.

The results are presented in FIG. 5. Each sample was administrated in 5 µl dose into each the left and right cerebral ventricles of mice.

In the following, the sample with the AD patient CSF plus the vehicle will be identified by the notation "vehicle-AD CSF". Similar notations are used for other samples.

As shown in FIG. 5, the mouse spontaneous alternation was significantly lower in the vehicle-AD CSF administered group than in the vehicle-Sham administered group.

On the other hand, the spontaneous alternation was higher in the 6E4HV0LV0-AD CSF administered group (final concentration of 10 ng/ml or 100 ng/ml) than in the vehicle-AD CSF administered group. The spontaneous alternation was particularly high in the 6E4HV0LV0-AD CSF administered group (final concentration of 100 ng/ml), recovering to the same levels as that observed in the vehicle-Sham administered group.

From these results and the results of Example 4, it was found that the impaired cognitive function observed in mice administered with AD patient CSF can be improved by the 6E4HV0LV0 intravenous administration and pretreatment.

Example 6

Blind Measurement of Mouse Cognitive Function Impairment by CSF Sample, and Blind Measurement of Changes in Cognitive Function of Mice after 6E4HV0LV0 Pretreatment The cognitive function of mice administered with multiple normal CSFs or AD patient CSFs was measured in blind experiment by performing a Y-maze test in the same manner as in Example 1. The effect of 6E4HV0LV0 pretreatment was also examined at the same time. The experiment was conducted by separating testers who is responsible for dispensing normal CSFs or AD patient CSFs and preparing a 6E4HV0LV0-pretreated AD patient CSF for blind experiment, and who is responsible for administering the samples to mice, and conducting the Y-maze test.

Tester (A) randomly assigned numbers to the dispensed normal CSFs (Precision Med) and AD patient CSFs (Precision Med) for blind experiment. For the AD patient CSFs, samples were also prepared by adding 6E4HV0LV0 to each dispensed CSF to make the final concentration 10 ng/ml, and incubating the mixture at room temperature for about 1 hour. The dispensed and prepared CSF samples were all preserved at −80° C. until the day of the Y-maze testing.

On the day of the Y-maze testing, tester (B) received the samples prepared by tester (A) for blind experiment, and thawed the samples at room temperature. Each sample (10 µl) or physiological saline (10 µl; hereinafter, "Sham") was administered into the cerebral ventricles of ICR mice under isoflurane anesthesia, and the mice were tested by Y-maze test in the same manner as in Example 1 to determine spontaneous alternation (%). The sample and the physiological saline were administrated in 5 µl dose into each of the left and right cerebral ventricles of mice.

The cognitive function of mice administered with the CSF sample that had no 6E4HV0LV0 pretreatment was determined as being impaired when the mouse spontaneous alternation decreased 3% or more compared with the Sham administered group. The cognitive function was determined as being strongly impaired when the spontaneous alternation decreased 7 to 10% compared to the Sham administered group. The results are shown under the column heading "Extent of induced cognitive function impairment" in Table 1 below.

Method of determining extent of induced cognitive function impairment is as follows.

−: The spontaneous alteration decreased 0 to 3% compared with the Sham administrated group (No induced cognitive function impairment).

+: The spontaneous alteration decreased 3 to 7% compared with the Sham administrated group (Weak induced cognitive function impairment).

++: The spontaneous alteration decreased 7 to 10% compared with the Sham administrated group (Strong induced cognitive function impairment).

A Y-maze test that used the AD patient CSFs pretreated with 6E4HV0LV0 was conducted at the same time. Percentage improvement of mouse spontaneous alternation by 6E4HV0LV0 pretreatment was calculated for each mouse by using the Formula (3) below. The results are shown under the column heading "Percentage improvement by 6E4HV0LV0 treatment (%)" in Table 1.

Percentage improvement (%) of mouse spontaneous alternation by 6E4HV0LV0 pretreatment={(spontaneous alternation of mouse administered with AD patient CSF pretreated with 6E4HV0LV0)−(spontaneous alternation of mouse administered with the same AD patient CSF without 6E4HV0LV0 pretreatment)}/{(spontaneous alternation of Sham administered group)−(spontaneous alternation of mouse administered with the same AD patient CSF without 6E4HV0LV0 pretreatment)}×100    Formula (3)

TABLE 1

| Patient ID | Age/Sex | Diagnosis | Extent of induced cognitive function impairment | Percentage improvement by 6E4HV0LV0 treatment (%) |
|---|---|---|---|---|
| 8006_Visit 3 | 91/male | AD | ++ | 80.2 |
| 8014_Visit 4 | 79/male |  | ++ | 59.7 |
| 8026_Visit 2 | 78/female |  | + | 14.5 |
| 8029_Visit 2 | 74/male |  | ++ | −11.8 |
| 8056_Visit 9 | 75/male |  | + | 86.8 |
| 8057_Visit 8 | 76/female |  | ++ | 59.3 |
| 8060_Visit 6 | 79/male |  | ++ | 46.0 |
| 8061_Visit 5 | 82/female |  | + | 65.6 |
| 8076_Visit 8 | 70/female |  | ++ | 68.3 |
| 8091_Visit 5 | 86/female |  | + | 56.3 |
| 8092_Visit 3 | 70/female |  | + | 87.7 |
| 8108_Visit 6 | 90/female |  | ++ | 82.0 |
| 8109_Visit 5 | 83/female |  | ++ | 90.7 |
| 8189_Visit 3 | 87/female |  | ++ | 83.1 |
| 8211_Visit 2 | 78/male |  | + | 90.0 |
| 7515_Visit 3 | 30/female | Normal | − |  |
| 7516_Visit 1 | 25/male |  | + |  |
| 7519_Visit 2 | 45/male |  | − |  |
| 7522_Visit 2 | 39/male |  | − |  |
| 7525_Visit 1 | 47/male |  | − |  |
| 7539_Visit 3 | 43/male |  | − |  |
| 7540_Visit 3 | 46/male |  | − |  |
| 7545_Visit 1 | 47/male |  | − |  |
| 7547_Visit 2 | 42/female |  | − |  |
| 7548_Visit 1 | 41/female |  | − |  |
| 7552_Visit 3 | 40/male |  | − |  |

As shown in Table 1, the mouse cognitive function was impaired in all of the 15 sample mice administered with the AD patient CSF that had no 6E4HV0LV0 pretreatment. On the other hand, 10 out of the 11 mice administered with the normal CSF did not show cognitive function impairment.

With regard to the effect of 6E4HV0LV0 pretreatment, the spontaneous alternation improved 80% or more in 7 out of the 15 samples, and 40% or more in 6 out of the 15 samples.

The cognitive function was impaired in 1 out of the 11 mice administered with the normal CSF. Percentage improvement (%) of mouse spontaneous alternation by 6E4HV0LV0 pretreatment was measured for the normal CSF administered to the mouse as for the AD patient CSF. However, the 6E4HV0LV0 pretreatment did not improve the cognitive function impairment occurred in this mouse.

It was found also from the foregoing blind tests that the cognitive function impairment was not induced in almost all mice administered with the normal CSF, but was induced in all the mice administered with the AD patient CSF. It was also found that most of the cognitive function impairment observed in mice administered with the AD patient CSF can show recovery with 6E4HV0LV0 pretreatment.

While the invention has been described in detail and with reference to specific embodiments thereof, it will be apparent to one skilled in the art that various changes and modifications can be made therein without departing from the spirit and scope of the invention. The present application is based on U.S. Provisional Application 61/980,206 filed on Apr. 16, 2014, and the contents are incorporated herein by reference.

REFERENCE SIGNS LIST

A, B, C: Arms

SEQUENCE LISTING FREE TEXT

SEQ ID NO: 1
Description of artificial sequence: Amino acid sequence of the 6E4HV0LV0 heavy chain variable region
SEQ ID NO: 2
Description of artificial sequence: Amino acid sequence of the 6E4HV0LV0 light chain variable region
SEQ ID NO: 3
Description of artificial sequence: Amino acid sequence of the 6E4HV0LV0 heavy chain CDR1
SEQ ID NO: 4
Description of artificial sequence: Amino acid sequence of the 6E4HV0LV0 heavy chain CDR2
SEQ ID NO: 5
Description of artificial sequence: Amino acid sequence of the 6E4HV0LV0 heavy chain CDR3
SEQ ID NO: 6
Description of artificial sequence: Amino acid sequence of the 6E4HV0LV0 light chain CDR1
SEQ ID NO: 7
Description of artificial sequence: Amino acid sequence of the 6E4HV0LV0 light chain CDR2
SEQ ID NO: 8
Description of artificial sequence: Amino acid sequence of the 6E4HV0LV0 light chain CDR3

The invention claimed is:

1. A method for measuring a toxicity of human cerebrospinal fluid (CSF), comprising
administering human CSF into a cerebral ventricle of a rodent, and
evaluating a cognitive function of the rodent by using a behavioral technique,
wherein the evaluating is carried out at about one hour from the time of administering human CSF.

2. The method according to claim 1, wherein the cognitive function evaluation is an evaluation of a short-term memory of the rodent.

3. The method according to claim 1, wherein the behavioral technique is a Y-maze test.

4. The method according to claim 1, wherein a dosage of the human CSF administered into the cerebral ventricle of the rodent is 5 µl or more.

5. The method according to claim 1, wherein the rodent is a mouse.

6. The method according to claim 1, wherein a dosage of the human CSF is 5 to 10 µL per rodent.

7. The method according to claim 6, wherein the dosage is 10 µL per rodent.

8. The method according to claim 1, wherein the human CSF is administered by injection.

9. A method for determining Alzheimer's disease, comprising
administering human CSF into a cerebral ventricle of a rodent, and
evaluating a cognitive function of the rodent by using a behavioral technique,
wherein the evaluating is carried out at about one hour from time of administering human CSF.

10. The method according to claim 9, wherein the cognitive function evaluation is an evaluation of a short-term memory of the rodent.

11. The method according to claim 9, wherein the behavioral technique is a Y-maze test.

12. The method according to claim 9, wherein a dosage of the human CSF administered into the cerebral ventricle of the rodent is 5 µl or more.

13. The method according to claim 9, comprising comparing the cognitive function of a rodent administered with a control into the cerebral ventricle and the cognitive function of the rodent administered with the human CSF into the cerebral ventricle.

14. The method according to claim 9, wherein the rodent is a mouse.

15. The method according to claim 9, wherein a dosage of the human CSF is 5 to 10 µL per rodent.

16. The method according to claim 15, wherein the dosage is 10 µL per rodent.

17. The method according to claim 9, wherein the human CSF is administered by injection.

18. A method for measuring the medicinal effect of an agent for treating Alzheimer's disease, comprising
(a) collecting human CSF from a subject after the administration of the agent;
(b) administering the human CSF collected in the step (a) into a cerebral ventricle of a rodent; and
(c) evaluating a cognitive function of the rodent administered with the human CSF collected after the administration of the agent,
wherein said cognitive function evaluation is performed using a behavioral technique, and
wherein the evaluating is carried out at about one hour from the time of administering human CSF.

19. The method according to claim 18, wherein the cognitive function evaluation is an evaluation of the short-term memory of the rodent.

20. The method according to claim 18, wherein the behavioral technique is a Y-maze test.

21. The method according to claim 18, wherein the human CSF collected after the administration of the agent is administered into the cerebral ventricle of the rodent at a dose of 5 µl or more.

22. The method according to claim 18, wherein the agent for treating Alzheimer's disease is an anti-amyloid β oligomer antibody.

23. The method according to claim 18, wherein the agent for treating Alzheimer's disease is an antibody selected from the following (a) and (b):
(a) a monoclonal antibody in which complementarity determining region (hereinafter, "CDR") 1, CDR2, and CDR3 of the heavy chain variable region ("VH") of the antibody comprise the amino acid sequences represented by SEQ ID NOS: 3, 4, and 5, respectively, and CDR1, CDR2, and CDR3 of the light chain variable region ("VL") of the antibody comprise the amino acid sequences represented by SEQ ID NOS: 6, 7, and 8, respectively; and
(b) a monoclonal antibody in which the VH of the antibody comprises the amino acid sequence represented by SEQ ID NO: 1, and the VL comprises the amino acid sequence represented by SEQ ID NO: 2.

24. The method according to claim 18, wherein the rodent is a mouse.

25. The method according to claim 18, wherein a dosage of the human CSF is 5 to 10 µL per rodent.

26. The method according to claim 25, wherein the dosage is 10 µL per rodent.

27. The method according to claim 18, wherein the human CSF is administered by injection.

28. A method for measuring the medicinal effect of an agent for treating Alzheimer's disease, comprising
(a) collecting human CSF from a subject starting or continuously undergoing administration of the agent before and after the administration of the agent;
(b) administering each of the human CSFs of before and after the administration of the agent collected in the step (a) into the cerebral ventricle of a rodent; and
(c) comparing a cognitive function of the rodent administered with the human CSF of before the administration of the agent and a cognitive function of the rodent administered with the human CSF of after the administration of the agent,
wherein said cognitive function is evaluated using a behavioral technique, and
wherein the evaluating is carried out at about one hour from the time of administering human CSF.

29. The method according to claim 28, wherein a dosage of the human CSF is 5 to 10 µL per rodent.

30. The method according to claim 29, wherein the dosage is 10 µL per rodent.

31. The method according to claim 28, wherein the human CSF is administered by injection.

32. The method according to claim 28, wherein the cognitive function evaluation is an evaluation of the short-term memory of the rodent.

33. The method according to claim 28, wherein the behavioral technique is a Y-maze test.

34. The method according to claim 28, wherein the human CSF collected after the administration of the agent is administered into the cerebral ventricle of the rodent at a dose of 5 µl or more.

35. The method according to claim 28, wherein the agent for treating Alzheimer's disease is an anti-amyloid β oligomer antibody.

36. The method according to claim 28, wherein the agent for treating Alzheimer's disease is an antibody selected from the following (a) and (b):
   (a) a monoclonal antibody in which complementarity determining region (hereinafter, "CDR") 1, CDR2, and CDR3 of the heavy chain variable region ("VH") of the antibody comprise the amino acid sequences represented by SEQ ID NOS: 3, 4, and 5, respectively, and CDR1, CDR2, and CDR3 of the light chain variable region ("VL") of the antibody comprise the amino acid sequences represented by SEQ ID NOS: 6, 7, and 8, respectively; and
   (b) a monoclonal antibody in which the VH of the antibody comprises the amino acid sequence represented by SEQ ID NO: 1, and the VL comprises the amino acid sequence represented by SEQ ID NO: 2.

37. The method according to claim 28, wherein the rodent is a mouse.

* * * * *